US006140058A

United States Patent [19]
Lane et al.

[11] Patent Number: 6,140,058
[45] Date of Patent: *Oct. 31, 2000

[54] ACTIVATION OF P53 PROTEIN

[75] Inventors: David Philip Lane, St. Andrews; Theodore Robert Hupp, Dundee, both of United Kingdom

[73] Assignee: Newburn Ellis, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/446,668

[22] PCT Filed: Nov. 26, 1993

[86] PCT No.: PCT/GB93/02438

§ 371 Date: Jul. 24, 1995

§ 102(e) Date: Jul. 24, 1995

[87] PCT Pub. No.: WO94/12202

PCT Pub. Date: Jun. 9, 1994

[30] Foreign Application Priority Data

Nov. 26, 1992 [GB] United Kingdom ................... 9224784

[51] Int. Cl.[7] ........................ G01N 33/53; G01N 33/574; A61K 39/395; C07K 1/00
[52] U.S. Cl. ...................... 435/7.1; 435/7.23; 424/155.1; 424/174.1; 530/350; 530/358
[58] Field of Search .............................. 424/155.1, 174.1; 435/7.1, 7.23, 21, 6; 436/64; 530/350, 358

[56] References Cited

FOREIGN PATENT DOCUMENTS 0475 623A1  3/1992  European Pat. Off. .
93 21529   10/1993  WIPO .

OTHER PUBLICATIONS

Dermer. G. B. "Another anniversary for the war on cancer" Bio/Technology, vol. 12, p. 320, Mar. 1994.
Gura, T. "Systems for identifying new drugs are often faulty" Science. vol. 278. pp. 1041–1042, Nov. 1997.
Lane, D. P., "A death in the life of p53", *Nature*, 362:786–787 (1993).
Hupp, T. R., "Regulation of the Specific DNA Binding Function of p53", *Cell*, 71:875–886 (1992).
Hupp, T. R., et al., "Activation of the cryptic DNA binding function of mutant forms of p53", *Nucleic Acids Research*, 21(14):3167–3174 (1993).
Gannon, J. V., et al., "Activating mutations in p53 produce a common conformational effect. A monoclonal antibody specific for the mutant form", *The EMBO Journal*, 9(5):1595–1602 (1990).
Hupp, T. R., et al., "Activation of the cryptic DNA binding function of mutant forms of p53", *Chemical Abstract, General Biochem.*, 119(13):333 (1993).
Gannon, J. V., et al., "Activating mutations in p53 produce a common conformational effect. A monoclonal antibody specific for the mutant form.", *Chemical Abstracts*, 113:166 (1990).

Hwang, D. S., et al., "Aggregated dnaA Protein Is Dissociated and Activated for DNA Replication by Phospholipase or dnaK Protein", *The Journal of Biological Chemistry*, 265(31):19244–19248 (1990).
Hall, P. A., et al., "High levels of p53 protein in UV–irradiated normal human skin", *Oncogene*, 8:203–207 (1993).
Kastan, M. B., et al., "Participation of p53 Protein in the Cellular Response to DNA Damage", *Cancer Research*, 51:6304–6311 (1991).
Milner, J., et al., "Cotranslation of Activated Mutant p53 with Wild Type Drives the Wild–Type p53 Protein into the Mutant Conformation", *Cell*, 65:765–774 (1991).
Bargonetti, J., et al., "Wild–Type but Not Mutant p53 Immunopurified Proteins Bind to Sequences Adjacent to the SV40 Origin of Replication", *Cell*, 65:1083–1091 (1991).
Hunter, T., et al., "The Regulation of Transcription by Phosphorylation", *Cell*, 70:375–387 (1992).
Livingston, L. R., et al., "Altered Cell Cycle Arrest and Gene Amplification Potential Accompany Loss of Wild–Type p53", *Cell*, 70:923–935 (1992).
Yin, Y., et al., "Wild–Type p53 Restores Cell Cycle Control and Inhibits Gene Amplification in Cells with Mutant p53 Alleles", *Cell*, 70:937–948 (1992).
Lu, X, et al., "ras–Induced Hyperplasia Occurs with Mutation of p53, but Activated ras and myc Together Can Induce Carcinoma without p53 Mutation", *Cell*, 70:153–161 (1992).
Kastan, M. B., et al., "A Mammalian Cell Cycle Checkpoint Pathway Utilizing p53 and GADD45 Is Defective in Ataxia–Telangiectasia", *Cell*, 71:587–597 (1992).
Vogelstein, B., et al., "p53 Function and Dysfunction", *Cell*, 70:523–526 (1992).
El–Deiry, W. S., et al., "Definition of a consensus binding site for p53", *nature genetics*, 1:45–49 (1992).
Carroll, D., et al., "Regulating Cell Growth: Casein–kinase–II–dependent Phosphorylation of Nuclear Oncoproteins", *Cold Spring Harbor Symposia on Quantitative Biology*, pp 91–95 (1988).

(List continued on next page.)

*Primary Examiner*—Yvonne Eyler
*Assistant Examiner*—Jennifer Nichols
*Attorney, Agent, or Firm*—Richard F. Trecartin; Flehr Hohbach Test Albritton & Herbert LLP

[57] ABSTRACT

A class of mutant forms of p53 protein, such as His273 and Lys285, which are defective in conversion from the latent to the activated state by casein kinase II, but with the ability to be activated for specific DNA binding by the action of ligands such as monoclonal antibody PAb421 and heat shock protein DnaK. Activation of these mutants, which are found at high levels in certain types of tumour, can potentially lead to selective growth arrest and induction of apoptosis in the tumor cells. p53 can be constitutively activated also by deletion of the C-terminal 30 amino acids. p53 activated in this way, or by ligand binding, can be administered for the purposes of tumour or cell growth suppression.

17 Claims, 4 Drawing Sheets

OTHER PUBLICATIONS

Hainaut, P., et al. "Interaction of heat–shock protein 70 with p53 translated in vitro: evidence for interaction with dimeric p53 and for a role in the regulation of p53 conformation", *The EMBO Journal*, 11(10):3513–3520 (1992).

Borellini, F., et al., "Induction of Sp1–p53 DNA–binding Heterocomplexes during Granulocyte/Macrophage Colony–stimulating Factor–dependent Proliferation in Human Erythroleukemia Cell Line TF–1", *The Journal of Biological Chemistry*, 268(11):7923–7928 (1993).

Lane, D. P., et al., "p53: oncogene or anti–oncogene?", *Genes & Development*, 4:1–8 (1990).

Mulner–Lorillon, O., et al., "M–phase–specific cdc2 protein kinase phosphorylates the β subunit of casein kinase II and increases casein kinase II activity", *Eur. J. Biochem.*, 193:529–534 (1990).

Kandror, K. V., et al., "Casein kinase II from *Rana temporaria* oocytes/Intracellular localization and activity during progesterone–induced maturation", *Eur. J. Biochme.*, 180:441–448 (1989).

Yonish–Rouach, E., et al., "p53–Mediated Cell Death: Relationship to Cell Cycle Control", *Molecular and Cellular Biology*, 13(3):1415–1423 (1993).

Kraiss, S., et al., "Oligomerization of Oncoprotein p53", *Journal of Virology*, 62(12):4737–4744 (1988).

Oliner, J. D., et al., "Amplification of a gene encoding a p53–associated protein in human sarcomas", *Nature*, 358:80–83 (1992).

Farmer, G., et al., "Wild–type p53 activates transcription in vitro", *Nature*, 358:83–86 (1992).

Lane, D. P., "p53, guardian of the genome", *Nature*, 358:15–17 (1992).

Donehower, L. A., et al., "Mice deficient for p53 are developmentally normal but susceptible to spontaneous tumours", *Nature*, 356:215–221 (1992).

Levine, A. J., et al., "The p53 tumour suppressor gene", *Nature*, 351:453–457 (1991).

Stürzbecher, H–W., et al., "A C–Terminal α–helix plus basic region motif is the major structural determinant of p53 tetramerization", *Oncogene*, 7:1513–1523 (1992).

Milne, D. M., et al., "Mutation of the casein kinase II phosphorylation site abolishes the anti–proliferative activity of p53", *Nucleic Acids Research*, 20(21):5565–5570 (1992).

Maltzman, W., et al., "UV Irradiation Stimulates Levels of p53 Cellular Tumor Antigen in Nontransformed Mouse Cells", *Molecular and Cellular Biology*, 4(9):1689–1694 (1984).

Clarke, C. F., et al., "Purification of Complexes of Nuclear Oncogene p53 with Rat and *Escherichia coli* Heat Shock Proteins: In Vitro Dissociation of hsc70 and dnaK from Murine p53 by ATP", *Molecular and Cellular Biology*, 8(3):1206–1215 (1988).

Lees–Miller, S. P., et al., "Human Cells Contain a DNA–Activated Protein Kinase that Phosphorylates Simian Virus 40 T Antigen, Mouse p53, and the Human Ku Autoantigen", *Molecular and Cellular Biology*, 10(12):6472–6481 (1990).

Abate, C., et al., "Redox Regulation of Fos and Jun DNA–Binding Activity in Vitro", *Reports*, pp 1157–1161 (1990).

Meisner, H., et al., "Phosphorylation of transcriptional factors and cell–cycle–dependent proteins by casein kinase II", University of Massachusetts Medical School, Current Opinion in *Cell Biology*, 3:474–483 (1991).

Friedman, P. N., et al., "The p53 protein is an unusually shaped tetramer that binds directly to DNA", *Proc. Natl. Acad. Sci. USA*, 90:3319–3323 (1993).

Baudier, J., et al., "Characterization of the tumor suppressor protein p53 as a protein kinase C substrate and a S100b–binding protein", *Proc. Natl. Acad. Sci. USA*, 89:11627–11631 (1992).

Schärer, E., et al., "Mammalian p53 can function as a transcription factor in yeast", *Nucleic Acids Research*, 20(7):1539–1545 (1992).

Kern, S. E., et al., "Identification of p53 as a Sequence–Specific DNA–Binding Protein", *Science*, 252:1708–1711 (1991).

Kern, S. E., et al., "Oncogenic Forms of p53 Inhibit p53–Regulated Gene Expression", *Science*, 256:827–831 (1992).

Malkin, D., et al., "Germ Line p53 Mutations in a Familial Syndrome of Breast Cancer, Sarcomas, and Other Neoplasms", *Research Articles*, pp 1233–1238 (1990).

Shaw, P., et al., "Induction of apoptosis by wild–type p53 in a human colon tumor–derived cell line", *Proc. Natl. Acad. Sci. USA*, 89:4495–4499 (1992).

Seto, E., et al., "Wild–type p53 binds to the TATA–binding protein and represses transcription", *Proc. Natl. Acad. Sci. USA*, 89:12028–12032 (1992).

McBride, A. A., et al., Conserved cysteine residue in the DNA–binding domain of the bovine papillomavirus type 1 E2 protein confers redox regulation of the DNA–binding activity in vitro, *Proc. Natl. Acad. Sci. USA*, 89:7531–7535 (1992).

Soussi, T., et al., "Structural aspects of the p53 protein in relation to gene evolution", *Oncogene*, 5:945–952 (1990).

Milne, D. M., et al., "Phosphorylation of the p53 tumour–suppressor protein at three N–terminal sites by a novel casein kinase I–like enzyme", *Oncogene*, 7:1361–1369 (1992).

Kern, S. E., et al., Mutant p53 proteins bind DNA abnormally in vitro, *Oncogene*, 6:131–136 (1991).

Funk, W. D., et al., A Transcriptionally Active DNA–Binding Site for Human p53 Protein Complexes, *Molecular and Cellular Biology*, 12(6):2866–2871 (1992).

Shaulian, E., et al., "Identification of a Minimal Transforming Domain of p53: Negative Dominance through Abrogation of Sequence–Specific DNA Binding", *Molecular and Cellular Biology*, 12(12):5581–5592 (1992).

Lamb, P., et al., "Characterization of the Human p53 Gene", *Molecular and Cellular Biology*, 6(5):1379–1385 (1986).

Bischoff, J. R., et al. "Human p53 Inhibits Growth in *Schizosaccharomyces pombe*", *Molecular and Cellular Biology*, 12(4):1405–1411 (1992).

Barak, Y., et al., "mdm2 expression is induced by wild type p53 activity", *The EMBO Journal*, 12(2):461–468 (1993).

Pinna, L. A., "Casein kinase 2: an 'eminence grise' in cellular regulation?", *Biochimica et Biophysica Acta.*, 1054:267–284 (1990).

Wade–Evans, A., et al., "Precise epitope mapping of the murine transformation–associated protein, p53", *The EMBO Journal*, 4(3):699–706 (1985).

Meek, D. W., et al., "The p53 tumour suppressor protein is phosphorylated at serine 389 by casein kinase II", *The EMBO Journal*, 9(10):3253–3260 (1990).

Xanthoudakis, S., et al., "Identification and characterization of Ref–1, a nuclear protein that facilitates AP–1 DNA–binding activity", *The EMBO Journal*, 11(2):653–665 (1992).

Xanthoudakis, S., et al., "Redox activation of Fos—Jun DNA binding activity is mediated by a DNA repair enzyme", *The EMBO Journal*, 11(9):3323–3335 (1992).

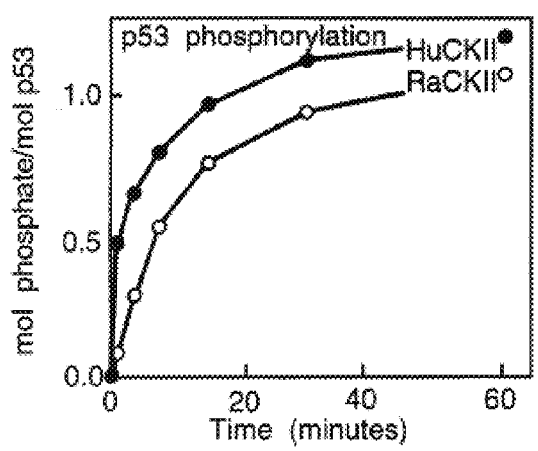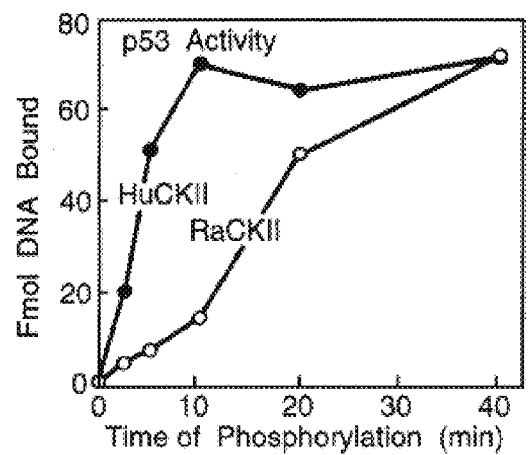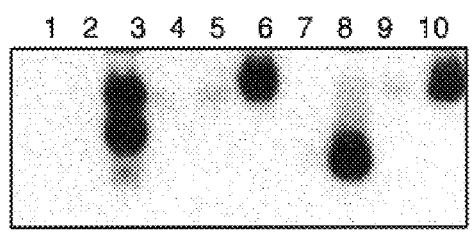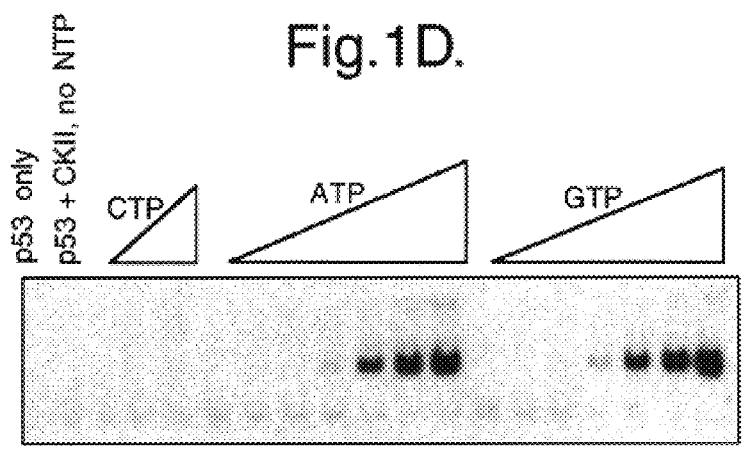

NEM sensitivity of PAb421-p53*

NEM sensitivity of DnaK-p53*

ACTIVATION OF P53 PROTEIN

FIELD OF THE INVENTION

This invention relates to the p53 tumour suppressor protein, and more particularly to mutant forms of the p53 protein which seem to be associated with certain types of tumour, and are usually found at elevated levels in such tumour cells. The invention also discloses the conversion of wild type p53 to a constitutively active form.

BACKGROUND TO THE INVENTION

Mutation of p53 is a very common genetic alteration in human cancers (1). Loss of the p53 tumour suppressor activity is co-incident with a loss of G1-S checkpoints following DNA damage (2), increases in genomic instability and selectable gene amplification (3,4). Mutant forms of p53 also appear to acquire a dominant growth promoting function (5,6). The region responsible for this transforming activity has been localized to a small C-terminal domain (7). Mice null for the wild type p53 locus develop normally, yet are susceptible to the development of neoplasia at elevated frequencies (8), indicating that wild type p53 is dispensable for the control over normal development and cell differentiation, but is essential to prevent spontaneous tumour formation. Consistent with this data, inherited germline point mutations in p53 lead to a predisposition to cancer in humans (9).

Wild type p53 protein levels rise dramatically in response to the DNA-damaging agents mitomycin C (56) UV light (10,11) and γ irradiation (2). Biochemical characterization of wild type p53 protein has shown that p53 can function as a sequence-specific DNA binding protein (12,13) and a transcription factor (14–16). These results support a model for wild type p53 in which its function is activated post-translationally after DNA damage to allow DNA repair by controlling the expression of regulatory gene products (18). These may include the DNA damage inducible gene gadd45 (19) and the host protein with oncogenic properties mdm-2 (20).

Biochemical characterization of p53 has become possible recently owing to the use of protein expression systems which allow for an abundant source of the protein. p53 purified using immunoaffinity chromatography has been shown to be a sequence-specific DNA binding protein which recognizes a motif containing two contiguous monomers of the sequence $(Pu)_{3-}C(A/T)(A/T)G(Py)_3$ (SEQ ID NO:8) (21). Sequence-specific DNA binding activity is manifested in the ability of p53 to bind the SV40 origin of replication (13), and by its ability to activate transcription in vitro from templates harbouring its DNA binding sequence (22). Mutant forms of p53 are defective in non-specific DNA binding (23), sequence-specific DNA binding (21) and transcriptional activation (14) suggesting that this activity is normally required to suppress tumour formation.

Phosphorylation of nuclear DNA binding proteins is an effective mechanism through which gene expression is controlled in response to environmental cues (24). Multi-site phosphorylation of p53 by protein kinases (25–27) suggests its tumour suppressor activity may be tightly co-ordinated by complex signal transducing pathways.

Casein kinase II (CasKII) is a highly conserved calcium and nucleotide independent enzyme which phosphorylates a broad spectrum of substrates, including transcription factors and DNA binding proteins (28). The activity of the kinase is stimulated in cells exposed to a variety of mutagens and growth factors (29). Mouse (25) and human p53 (17) are phosphorylated at the penultimate C-terminal amino acid by Cas KII in vitro. Mutation of this highly conserved C-terminal serine residue of mouse p53 to an alanine abolishes the growth suppressive function of the protein in mammalian cells, suggesting that phosphorylation at this site is one important modification required to activate the tumour suppressor function of p53 (30). Based on biochemical and physiological data, CasKII is the only known enzyme involved in a direct and positive regulation of the activity of p53.

Understanding the regulation of p53 activity is a vital step for the development of therapeutic strategies designed to restore tumour suppressor activity of the protein in transformed cells. Using in vitro systems, it has already been established that wild type p53 activity is negatively regulated in vitro by the viral oncogene, T-antigen (22), and host associated oncogene mdm-2 (31).

It appears that sequence specific DNA binding is one activity of p53 required for its tumour suppressor function. To date, all mutant forms of p53, eg those encoded by the hotspot alleles, His175, Trp248, and His273, have been shown to be defective in sequence specific DNA binding (21) and in the activation of transcription from templates harbouring its consensus DNA binding site (14).

SUMMARY OF THE INVENTION

Enzymatic modulation of p53 may provide a framework from which to couple signal transducing pathways with the P53 response to DNA damage and ultimately growth control. To study the effects of p53 phosphorylation on the activity of the protein, we have purified unmodified recombinant p53 by conventional chromatography from bacteria and shown it to be a multimeric protein which is latent for sequence specific DNA binding (17). A motif within the C-terminal 30 amino acids negatively controls p53 function as deletion of this domain constitutively activates p53. A set of p53 activating proteins, including rabbit muscle casein kinase II, monoclonal antibody PAb421, and *E.coli* Hsp70, target this C-terminal domain.

We have therefore shown that while sequence specific DNA binding activity is cryptic, it can be unmasked by enzymes and proteins, including casein kinase II (17). From the observation that p53 is regulated positively by CasKII, we attempted to determine if some mutant forms of p53 are inactive in DNA binding as a result of a defect in conversion from a latent to an activated state.

Mutant forms of p53 encoded by common 'hotspot' alleles were purified and their activities were characterized at the biochemical level. We show here that two mutant forms of p53 encoded by the His273 and Lys285 alleles are not inherently defective in sequence-specific DNA binding, but appear to prefer residence in the latent state. A monoclonal antibody and *E.coli* DnaK are able to promote sequence-specific DNA binding by these mutant forms of P53, but the most potent physiological activator CasKII is unable to effectively unmask the DNA binding function.

A new biochemical class of mutant forms of p53 is thus established which is defective in DNA binding after post-translational modification by the growth controlling enzyme CasKII. This class of mutant p53, defective in the conversion from the latent to the activated state, was our target for the construction of molecules with the ability to reactivate the tumour suppressor function of mutant p53, and thus potentially lead to selective growth arrest and induction of apoptosis in tumour cells (32,33).

According to one aspect of the invention, there is provided a method which comprises activating a mutant p53 protein for specific DNA binding by the action of a ligand which binds to the mutant p53, wherein said mutant has the properties that (i) it occurs at elevated levels in tumours, (ii) it does not substantially suppress tumour growth, (iii) it is not substantially activated by CasKII mediated phosphorylation.

The mutant p53 will be likely to involve amino acid substitution of the wild-type p53 outside the C-terminal 30 amino acids. Examples are mutants in which the substitution is at either or both of positions 273 and 285, typically producing his273 and lys285.

The activation typically is mediated by the action of a ligand which binds to the mutant p53 within the C-terminal 30 amino acids. Suitable such ligands are the monoclonal antibody PAb421 or the bacterial heat shock protein DnaK, but it is contemplated that activation will also be mediated by a ligand which binds effectively to the same site on the mutant p53. Such equivalent ligand may comprise a binding peptide fragment of PAb421 or DnaK, or it may be a molecular "mimetic" thereof.

The designing of mimetics to a known pharmaceutically active compound is a known approach to the development of pharmaceuticals based on a "lead" compound. Typically, the three-dimensional structure of the ligand and its binding to the receptor is modelled, generally using a computer, and alternative molecules are devised for the ligand which have the same or equivalent binding regions, but which may differ markedly from the original ligand in other respects. For example, the original ligand may be a protein or peptide, but the mimetic may be a non-peptide molecule having a quite different skeleton but which has atoms or groups at the receptor binding locations which have the same sort of characteristics, such as size, electric charge, hydrophobicity etc, as the corresponding parts of the original ligand. In this way, a mimetic can be devised which fulfils the same binding and pharmacologic function as the original ligand, but is for example easier to manufacture and formulate as a pharmaceutical agent.

According to another aspect of the invention, there is provided a pharmaceutical composition for activating mutant p53 for specific DNA binding, wherein said mutant has the properties that (i) it occurs at elevated levels in tumours, (ii) it does not substantially suppress tumour growth, (iii) it is not substantially activated by CasKII mediated phosphorylation, the composition comprising a ligand capable of binding to the mutant p53 and activating it, and a suitable excipient.

The ligand used in the composition suitably has the characteristics described above.

A further aspect of the present invention lies in the use of constitutively activated p53, whether wild type or mutant, for therapeutic purposes, as in the tumour or cell growth suppression. Constitutive activation can be by the binding of a ligand such as PAb421 or DnaK, or the deletion of a C-terminal region, typically the 30 C-terminal amino acids of the full length molecule; the precise limits of what can be deleted to obtain the effect can of course be determined by routine experimentation.

DEFINITIONS

PAb421 is a known monoclonal antibody (Harlow et al, J Virol (1981), vol 37, 564–573) and is available from Oncogene Sciences, NY, USA. It has been found to bind to the amino acid motif SKKGQSTSRHK (SEQ ID NO:1) in the C-terminal region of p53. Contemplated within the terms of this invention are other antibodies, binding fragments thereof, or non-antibody ligands, natural or synthetic, that are able to compete with PAb421 for binding to that motif and activating mutant p53s. Another monoclonal antibody that recognises the same site and can activate mutant p53 is PAb122 (Gurney et al, J Virol (1980), vol 34, 752–763), and is available through the ATCC under deposit No ATCC TIB 116.

DnaK is a known protein (Huang et al, J Biol Chem (1991), vol 266, 7537–7541) and is available from Stress-Gen Biotechnologies Corp, Victoria, BC, Canada. It is a bacterial heat shock protein found in $E\ coli$, and has been found to bind to the amino acid motif RHKKLMFTKTE (SEQ ID NO:2) in the C-terminal region of p53. Contemplated within the terms of this invention are other ligands, natural or synthetic, able to compete with DnaK for binding to that motif and activating mutant p53s.

DO-1 is a known monoclonal antibody (Vojtisek et al, J Immunol Meth (1992), vol 151, 237–244).

DESCRIPTION OF THE DRAWINGS

FIGS. 1A–1D: Rate of phosphorylation of p53 by native and recombinant casein kinase II. p53 (50 ng) was phosphorylated at 30° C. in DNA binding buffer (in the absence of an ATP regeneration system and DNA) for the indicated times using recombinant human casein kinase II (HuCKII; 125 ng) or native rabbit muscle casein kinase II (RaCKII; MonoQ fraction; 375 ng). Reaction products were separated by SDS gel electrophoresis. Radiolabeled p53 was excised from the gel and radioactive phosphate was quantified by scintillation counting. Activity is expressed as the moles of phosphate incorporated per mole of p53 monomer. (B). Rate of activation of p53 DNA binding by rabbit muscle or recombinant casein kinase II. p53 (50 ng) was phosphorylated at 30° C. for the indicated times (in the absence of an ATP regeneration system and DNA) using rabbit muscle (RaCKII; MonoQ fraction, 375 ng) or recombinant casein kinase II (HuCKII, 125 ng). Radiolabeled DNA was added and reactions were incubated at 0° C. for 5 minutes, followed by gel electrophoresis. Radiolabelled p53-DNA complexes were scanned and quantified using a phosphoimager. Activity is expressed as the Fmoles of DNA bound by 50 ng of p53 as a function of the time of phosphorylation for 40 minutes with different amounts of rabbit muscle or recombinant casein kinase II as in parts A and B. Reaction products were separated by electrophoresis on a 4% polyacrylamide gel; Lane 1(p53+1.2 ng of HuCKII), lane 2 (p53+12.5 ng of HuCKII), lane 3 (p53+125 ng of HuCKII), lanes 4–6 (as in lanes 1–3, but with the addition of DO-1 after DNA binding), lane 7 (p53+37 ng of RaCKII), lane 8 (p53+375 ng of RaCKII), lanes 9 and 10 (as in lanes 8 and 9, but with DO-1 added after activation of DNA binding). (D) GTP replacement of ATP in the activation of p53. Complete reactions (without an ATP regeneration system and DNA) containing 50 ng of p53 and 375 ng of native casein kinase II were assembled without nucleotide. The indicated nucleotide was added and incubations were at 30° C. for 40 minutes. After the addition of the DNA binding mixture, reaction products were analyzed. Reading from left to right; lane 1 (p53 only, with 1 mM ATP), lane 2 (p53 and CK II, without NTP), lane 3–5 (p53 and CK II, with 62,250 and 1000 $\mu$M ATP, respectively), lanes 6–12 (p53 and CKII, with 0.24, 0.97, 3.4, 15, 62, 250, and 100 $\mu$M ATP respectively), lanes 13–19 (as in 6–12, but using GTP in place of ATP).

DETAILED DESCRIPTION OF THE INVENTION

Figure 2A:
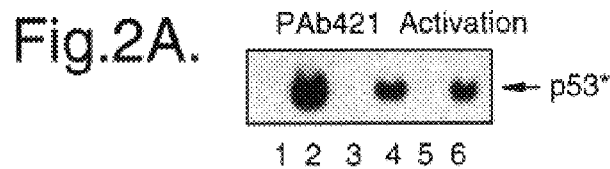
FIGS. 2A–2D: Activation of sequence-specific DNA binding of wild type and mutant p53. Activation reactions were staged in two parts. In the first stage, wild type p53 (60 ng) or mutant forms of p53 (180 ng) was incubated with ATP and the indicated activating protein at 30° C. for 30 minutes. In the second stage, the consensus site oligonucleotide was added to the reactions to assay for sequence-specific DNA binding. (A) PAb421; lane 1, 3 and 5 (p53, p53 His 273, and p53 Lys285, respectively), lanes 2, 4 and 6 (PAb421 and p53, p53 His273, and p53 Lys285, respectively). (B) DnaK; lanes 1, 5, and 9 (p53, p53 His273, and p53 Lys285, respectively), lanes 2, 6 and 10 (DO-1 and p53, p53 His273, and p53 Lys285, respectively), lanes 3, 7 and 11 (DnaK and p53, p53 His273, and p53 Lys285, respectively), lanes 4, 8 and 12 (DnaK and p53, p53 His273, and p53 Lys285, respectively, followed by DO-1). (C) Casein Kinase II; lanes 1, 5, and 9 (p53, p53 His273, and p53 Lys285, respectively), lanes 2, 6 and 10 (DO-1 and p53, p53 His273, and p53 Lys285, respectively), lanes 3, 7 and 11 (Casein Kinase II and p53, p53 His273, and p53 Lys285, respectively), lanes 4, 8 and 12 (Casein Kinase II and p53, p53 His273, and p53 Lys285, respectively, followed by DO-1). p53* marks the migration of the activated p53-DNA complex. (D) Specific activity of wild type and mutant p53. PAb421-activated p53 (solid bar), DnaK-activated p53 (open bar), casein kinase II-activated p53 (stippled bar). The specific activities of wild type, His273 and Lys285 are indicated.

We have already demonstrated (Reference 17: Hupp et al, Cell, Vol 71, 875–886, Nov. 27, 1992) that the DNA binding activity of p53, required for its tumour suppressor function, is cryptic but can be activated by cellular factors acting on a C-terminal regulatory domain of p53. A gel mobility shift assay demonstrated that recombinant wild-type human p53 binds DNA sequence specifically only weakly, but monoclonal antibody PAb421 binding near the C-terminus activated the cryptic DNA binding activity stoichiometrically. p53 DNA binding could also be activated by a 30 amino acid C-terminal deletion of p53 (deletion of 90 amino acids inactivated it), mild proteolysis of full length p53 (with trypsin), E coli DnaK (which disrupts protein-protein complexes) or CasKII (and coincident phosphorylation of a C-terminal site on p53). All the foregoing is described in more detail in the Hupp et al paper, to which reference may be made as appropriate.

Using an in vitro system coupling post-translational modification of wild type p53 to the activation of sequence specific DNA binding, we have examined the effect of mutation on the latent DNA binding function of p53. Purification and biochemical characterization of mutant forms of p53 from bacterial expression systems demonstrated that a set of mutants share fundamental properties with the wild type protein.

Like wild type p53, the purified mutants encoded by the His273 and Lys285 alleles (i) appear to exist as latent multi-protein complexes and can be converted to active DNA binding forms by PAb421 and DnaK; (ii) express the N-terminal epitopes recognized by monoclonal antibody DO-1 in the native p53-DNA complex; (iii) require reactive sulfhydryl to promote sequence-specific DNA binding; and (iv) are effectively phosphorylated by CasKII in vitro.

There is however, one noticeable difference between these two mutant proteins and wild type p53. It appears that the mutants are severely defective in the GTP or ATP dependent activation of sequence-specific DNA binding by the cellular enzyme CasKII. Given that wild type p53 is regulated positively by phosphorylation, implicating CasKII involvement in the p53 pathway (52), it is reasonable to expect that defects in this modulation would result in the net loss of p53 tumour suppressor activity. This defect would be made manifest in perturbation of the CasKII signal transducing pathway, in which hypophosphorylated p53 would be inactive as a tumour suppressor. In the selection for mutation during the process of cellular transformation, there could be a selection for: (i) a p53 mutation in the CasKII recognition site at the C-terminus, which would prevent post-translational modification by the kinase, (ii) a dominant p53 mutation in exon 11 which would strengthen the activity of the negative regulatory domain, effectively locking p53 into the latent state, or (iii) a p53 mutation outside the C-terminal domain which confers an immunity to activation after phosphorylation. The two mutants exemplified herein fall into the latter class. Mutations residing in the C-terminus may exist, but since this region is not highly conserved, little emphasis has been placed on screening p53 alleles for mutation in this negative regulatory domain.

EXPERIMENTAL PROCEDURES

A. Materials and Methods

Enzymes and Reagents

Purified fractions of recombinant human wild type p53 and p53Δ30 from a bacterial expression system, p53 specific monoclonal antibodies PAb421 and DO-1 were obtained as described previously (17). Mutant forms of p53 encoded by the Lys285 and His273 alleles were purified from a bacterial expression system using Heparin Sepharose and Gel filtration chromatography as described for wild type p53. Fractions containing mutant p53s eluting at approximately 440 Kd on gel filtration (compared to protein standards) and which could be activated for sequence-specific DNA binding by PAb421 were concentrated using a Centricon-30 (Amersham) to 0.5 mg/ml and stored frozen at −70° C. Mutant forms of p53 purified by this method were greater than 90% pure when stained with Coomasie Blue in an SDS polyacrylamide gel.

The $E.coli$ Hsp70 homologue (DnaK) was purified from an overproducing strain by a modification of the published protocol (49). Active fractions of DnaK eluting from MonoQ (49) were applied to an ATP-Agarose column in Buffer P (10% glycerol, 25 mM HEPES (pH 7.6), 0.1 mM EDTA, and 1 mM DTT) containing 10 mM $MgCl_2$. After a 10 column volume wash in Buffer P containing 1.0 M KCl+10 mM $MgCl_2$ and a 5 column volume wash with Buffer P containing 10 mM KCl+10 mM $MgCl_2$, bound DnaK was eluted with Buffer P containing 10 mM $MgCl_2$+5 mM ATP. The fractions of DnaK eluting from ATP agarose were dialyzed overnight at 3° C. against Buffer P containing 2 mM EDTA and 0.25 M KCl. DnaK was further purified on Superose-12 gel filtration equilibrated in Buffer P containing 0.25 M KCl. NEM and Diamide were from Sigma.

Sources of Casein Kinase II

CasKII from rabbit muscle was purified as described (17) with the following modifications. Muscle from a rabbit was ground in 2 liters of homogenization buffer (4 mM EDTA, 2 mM DTT, 1 mM Benzamidine) and centrifuged at 4000×g for 45 minutes. The soluble supernatant containing 27.5 grams of protein was batch adsorbed to 200 ml of phosphocellulose resin in Buffer P for 2 hours. The column was washed with Buffer P containing 0.35 M KCl, and CasKII activity was step eluted with Buffer P containing 1.2 M KCl and 0.1% Triton X-100. After Phosphocellulose, fractions containing CasKII were applied to a Heparin Sepharose column and eluted with a linear gradient from 0.05 to 1 M KCl in Buffer P containing 0.1% Triton X-100. Active fraction were applied to a MonoQ column and eluted with a linear KCl gradient in Buffer P containing 0.1% Triton X-100. Active CasKII was concentrated to 0.75 mg/ml using Centricon-30 and stored at 4° C. Kinase activity was monitored by assaying for radioactive phosphate incorporation into p53 and casein as described (17). Casein and p53 kinase activities were co-incident after Heparin Sepharose and MonoQ chromatography. Recombinant human CasKII holoenzyme expressed in $E.coli$ was 95% pure and was obtained from Boehringer Mannheim.

Synthesis of oligonucleotides and preparation of duplex substrates

Oligonucleotides containing the 20-mer p53 consensus DNA binding site (PG) (22) and Hind III compatible ends were: 5' AGC TTA GAC ATG CCT AGA CAT GCC TA 3' (SEQ ID NO:4) and 5' AGC TTA GGC ATG TCT AGG CAT GTC TA 3' (SEQ ID NO:5). Oligonucleotides without the consensus sequence (TL) were: 5' TAT GTC TAA GGG ACC TGC GGT TGG CAT TGA TCT TG 3' (SEQ ID NO:6) and 5' GTG CCA AGA TCA ATG CCA ACC GCA GGT CCC TTA GAC A 3' (SEQ ID NO:7). Complementary oligonucleotides were hybridized and end-labelled with $^{32}$P-γ-ATP as described (Maniatis et al, 1982) and stored at 4° C.

p53 Sequence-specific DNA Binding Using a Gel Mobility Shift Assay

A 20 μl reaction volume contained DNA binding buffer (20% glycerol, 25 mM HEPES (pH 7.6), 50 mM KCl, 1 mM DTT, 1 mg/ml BSA and 0.1% Triton X-100) and was mixed with PG radiolabelled DNA, unless indicated otherwise (1–5 ng), competitor DNA (20–100 ng of pBluescript II), the indicated amounts of p53 (Fraction III) and the indicated p53-specific monoclonal antibodies. Incubations followed a 0° C. for 30 minutes unless indicated otherwise. Reaction products were loaded onto a 4% polyacrylamide gel containing 0.33×TBE and 0.1% Triton X-100, which had undergone pre-electrophoresis at 100V for 15 minutes at 3° C. Electrophoresis was continued at 200V from 30 to 90 minutes at 3° C. Gels were dried prior to exposure to X-ray film.

Phosphorylation of p53

Reactions (10 μl) contained DNA buffer (without DNA) supplemented with 100 μM ATP containing $^{32}$P-γ-ATP, and 125 ng of p53 (Fraction III). CasKII obtained after gel filtration (80 ng) was added and after incubations at 30° C. for the indicated times, reactions were quenched by the addition of SDS-PAG sample buffer. Products were separated by electrophoresis on a 10% SDS-polyacrylamide gel. p53 was localised by staining with Coomassie Blue and the bands were excised and counted using a liquid scintillation counter (Beckmann LS 1801).

Activation of p53 by CasKII and DnaK

Reactions (10 μl) contained DNA binding buffer (without DNA) supplemented with 30 ng of p53 (Fraction III), 1 mM ATP, and with an ATP regenerating system containing 0.1 mg/ml creatine kinase II and 20 mM phosphocreatine. After the addition of the indicated amounts of CasKII or purified DnaK, reactions were incubated at 30° C. for 30 minutes. A 2-fold concentrated mixture containing radiolabelled DNA, competitor DNA, and the indicated monoclonal antibodies (10 μl) was added and incubations were continued at 21° C. for 10 minutes. Reaction products were analysed as described above.

Activation of Wild Type or Mutant Forms of p53

Activation of the sequence-specific DNA binding function of wild type and mutant forms of p53 were performed using the assay conditions previously described with the following modifications. In a 10 μl reaction containing 20% glycerol, 25 mM HEPES (pH 7.6), 0.05% Triton X-100, 5 mM Mg $Cl_2$, 50 mM KCl, 0.1 mM EDTA, 1 mg/ml BSA, 0.1 mg/ml creatine kinase, 20 mM phosphocreatine, 1 mM ATP, the indicated amounts of wild type or mutant p53 and the indicated activating protein, reactions were incubated at 30° C. for 30 minutes. A 10 µl aliquot containing the radiolabeled consensus DNA binding oligonucleotide (5' AG-CTT AGACATGCCT AGACATGCCT A 3' (SEQ ID NO:4)) and 5' AGCTTAGGCATGTCT AGGCATGTCT A 3' (SEQ ID NO:5) ) defined by El-Deiry (21) with competitor plasmid DNA was added and reactions were incubated at 30° C. for 5 minutes. Unless indicated otherwise, PAb421 (400 ng), DnaK (2 µg), CasKII (240 ng), or DO-1 (400 ng) were added. Reaction products were separated by electropohoresis in a native 4% polyacrylamide gel containing 0.1% Triton X-100 and 0.33×TBE at 3° C.

B. Results

The bacterial and mammalian cell expression of p53 exhibiting sequence specific DBA binding, activation of wild-type p53 by Fab421, DnaK or CasKII, and by limited tryptic digestion or by C-terminal deletion.

These results, and the details of the experiments, are provided in our paper Hupp et al (17).

Activation of Mutant Forms of p53 by PAb421 and DnaK

Our recent identification of the latent biochemical phenotype of wild type p53 (17) supports the possibility that some mutant forms of p53 may be inactive due to a relative defect in activation of DNA binding by a post-translational modification (FIG. 5). Identification of such a class of mutant p53 would provide suggestive evidence for the importance of a CasKII signalling pathway in the cell and define a class of p53 which could presumably have the capacity to have its tumour suppressor function re-activated by alternative post-translational modifications.

To test this possibility, we have examined the behaviour of mutant forms of p53 in sequence-specific DNA binding assays. Mutant forms of p53 encoded by the His175, Trp248, His273, and Lys285 alleles were purified using Heparin Sepharose and gel filtration chromatography as described for wild type p53. The mutant proteins eluted as a multi-protein complex of approximately 440 Kd on gel filtration, similar to that observed with wild type p53 (17). These results indicate that the mutations have not prevented stable associations between monomers.

Figure 5A:
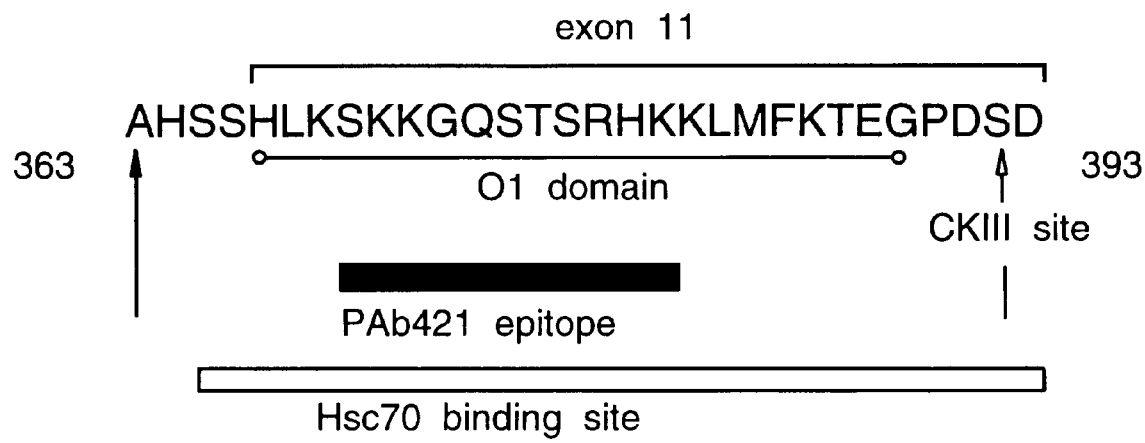
FIGS. 5A–5B: (A) C-terminal binding sites of the p53 binding proteins within exon 11(45). The 30 C-terminal amino acids from 363 to 393 (SEQ ID NO:3) are listed (46). Important motifs include: The O1 domain required for higher order oligomerization (38); the CKII phosphorylation site (open headed arrow) (47); the PAb421 binding site (48), the Hsc70 binding site (36), and the endpoint of p53Δ830 (closed arrow) (17). (B) Model describing the equilibrium shifts between dimeric p53 molecules in the latent or the activated states. The solid arrow indicates the direction favoured in the equilibrium for wild type or mutant p53s. Wild type p53 can be effectively converted to the active form by casein kinase II, PAb421, or DnaK. Conformational changes which occur after modification by the activating protein relieve the inhibition of DNA binding dependent upon C-terminal amino acids flanking the PAb421 binding site (stippled rectangle or ellipse). This conformational change activates the sequence specific DNA binding function. In contrast to the wild type protein, p53 mutants may be trapped in the latent state, even in the presence of activating proteins. Conditions that favour the interaction of activating proteins with p53 and that induce conformational changes in the C-terminus may activate the tumour suppressor function of mutant forms of p53.

Wild type p53 did not exhibit sequence-specific DNA binding unless activated by the monoclonal antibody, PAb421 (FIG. 2A, lane 2 vs.lane I). PAb421 binds to the C-terminus of p53 and presumably induces a conformational change that neutralizes the function of a negative regulatory domain (FIG. 5A). Highly purified mutant forms of p53 encoded by the His273 and Lys285 alleles were also unable to bind DNA sequence-specifically, but were effectively activated for DNA binding by PAb421 (FIG. 2A, lanes 4 and 6 vs. lanes 3 and 5). The specific activities for the mutant proteins were 6–8 fold lower than wild types p53 (See FIG. 2D and the following Table).

TABLE

Specific activity of activated wild-type and mutant p53s
(Fmol DNA bound/µg protein)

| p53 | PAb421 | DnaK | CasKII |
|---|---|---|---|
| wild type | 166 | 57 | 64 |
| His273 | 55 | 31 | 3.8 |
| Lys285 | 47 | 14 | 2.6 |

Figure 5B:
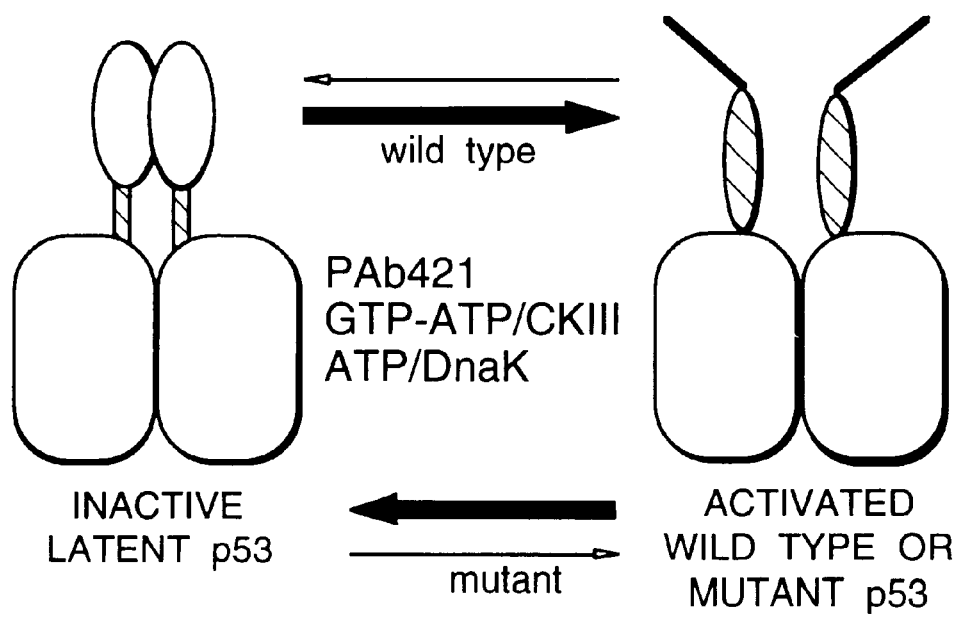

Apparently, these point mutations in p53 do not abolish sequence-specific DNA binding as the cryptic function can be activated (FIG. 5B). The other two common mutants studied, His175 and Trp248 could not be activated in DNA binding by PAb421 under these conditions, suggesting that the cryptic activity may be permanently locked into the latent state (FIG. 5B).

p53 can bind to DnaK and Hsc70 in vivo (35). Hsc70 binds to the C-terminus of p53 synthesized in reticulocyte lysates (36), suggesting that this family of proteins targets the same domain as PAb421 and CasKII (FIG. 5A). We have found that this interaction may have functional significance, since purified recombinant DnaK is able to activate sequence specific DNA binding of wild type P53.

Figure 2B:
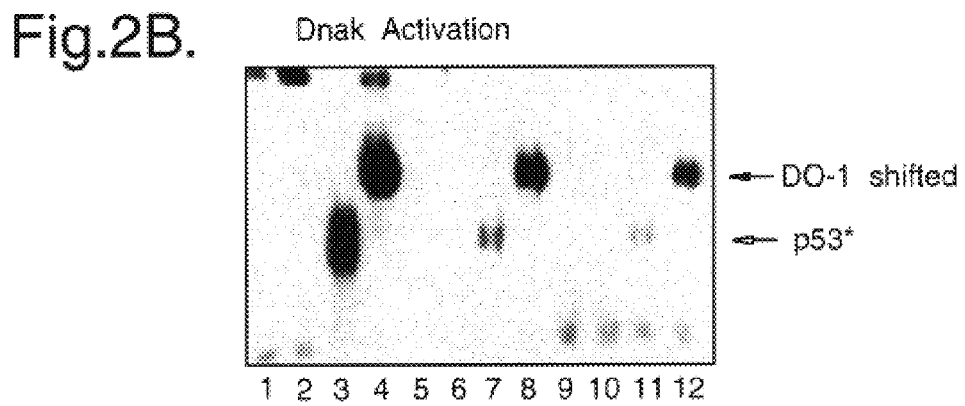
Figure 2C:
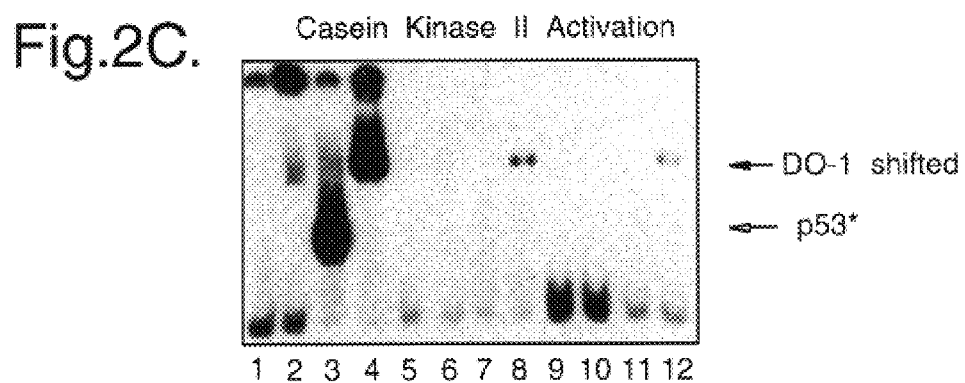
Figure 2D:
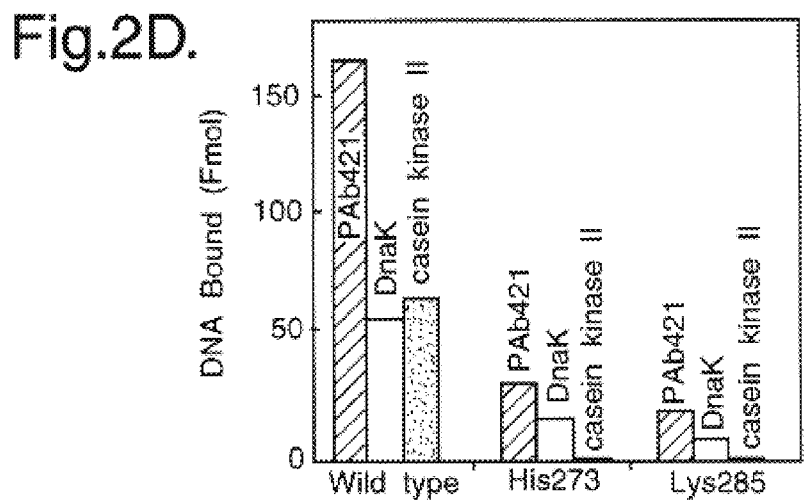

The His 273 and Lys285 mutant p53s were also activated by DnaK to give rise to products similar in mobility to activated wild type p53 (FIG. 2B, lanes 3, 7, and 11 vs. lanes 1, 5 and 9). A monoclonal antibody specific for the N-terminus of p53, DO-1, was able to supershift the DnaK activated wild type and mutant p53s (lanes 4, 8 and 12 vs. lanes 3, 7 and 11). DnaK activated mutant p53 bound by DO-1 are 4–6 fold less active than wild type p53 activated by this head shock protein (FIG. 2D). The enhancement of DnaK activated mutant p53 DNA binding function was observed upon the inclusion of DO-1 (FIG. 2B). The mutant forms of p53, though in an activated state, may yet favour equilibrium towards the latent state (FIG. 5), and the inclusion of DO-1 may help to lock the protein into the high affinity DNA binding conformation.

Mutant forms of p53 are Severely Defective in Activation by Casein Kinase II

The third protein which we have been using to activate wild type p53, and one which is presently the most physiologically relevant, is casein kinase II. The C-terminal CasKII phosphorylation site is required for tumour suppressor function is mammalian cells (30). Covalent modification of wild type p53 by CasKII in vitro is GTP or ATP dependent and activates the cryptic sequence-specific DNA binding function of P53 (FIG. 1). Although wild type p53 was activated very effectively by CasKII, both latent, mutant forms of p53 (FIG. 2C, lanes 3, 7 and 11 vs. lanes 1, 5 and 9; FIG. 2D) were activated to a very low extent by CasKII; this is more noticeable after the addition of DO-1, which supershifted the protein-DNA complexes (lanes 4, 8 and 12 vs. lane 2). Quantification of the products of DNA binding indicates that CasKII is 20–30 times less effective than PAb421 in activation of these two mutant forms of P53 (FIG. 2D). The mutant proteins were phosphorylated as effectively as wild type p53 by casein kinase II in vitro. This modification was inhibited by PAb421, indicating that phosphorylation is occurring within the C-terminus as is observed with wild type p53.

Figure 3A:
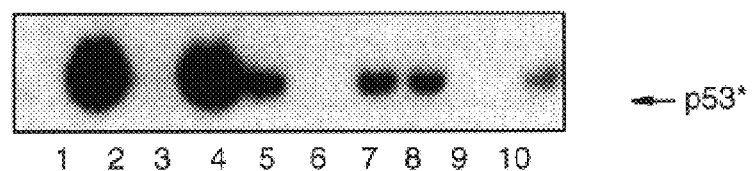
FIGS. 3A–3B: (A) NEM sensitivity of PAb421 activated p53. After PAb421 activation of wild type p53 (60 ng; lanes 2–4), p53 His273 (60 ng; lanes 5–7), and p53 Lys 285 (60 ng; lanes 8–10) as described in the methods, redox reagents were added (DTT to 2 mM or NEM to 1 mM) and incubations were continued at 30° C. for 10 minutes. Lane 1 (no protein), lanes 2, 5, and 8 (p53's-PAb421 only), lanes 3, 6 and 9 (p53's-PAb421 and NEM followed by DTT), lanes 4, 7, and 10 (p53's-PAb421 and DTT followed by NEM). Reactions were then incubated with the consensus DNA oligonucleotide to assay for sequence specific DNA binding as described in the methods. (B) NEM sensitivity of DnaK activated p53. After activation of p53 His273 (180 ng; lanes 1–3) and p53 (60 ng; lanes 4–6 as described in the methods, redox reagents were added and incubations were continued at 30° C. for 10 minutes. Lanes 1 and 4 (p53s only), lanes 2 and 5 (DnaK activated p53 with DTT, followed by NEM), lanes 3 and 6 (DnaK activated p53 with NEM followed by DTT). Incubations were then continued with the consensus DNA oligonucleotide to assay for DNA binding as described in the methods p53* marks the position of the activated p53-DNA complex.

Activated Wild Type and Mutant Forms of p53 both Require a Reactive Sulfhydryl for Sequence-specific DNA Binding Independent biochemical analysis of wild type p53 has shown that it requires reactive sulfhydryl for effective sequence specific DNA binding, and it was of interest to determine if the altered conformation of activated mutant forms of p53 could express this biochemical phenotype. In stage activation of wild type and mutant forms of p53 by PAb421, the inclusion of NEM after the activation step inhibited sequence specific DNA binding (FIG. 3A, lanes 3, 6 and 9 vs. lanes 2, 5 and 8). As with wild type p53, the prior inclusion of DTT followed by the addition of NEM prevented inhibition of DNA binding of the PAb421 activated mutant forms of p53 (lanes 4, 7 and 10 vs. lanes 3, 6 and 9).

Figure 3B:
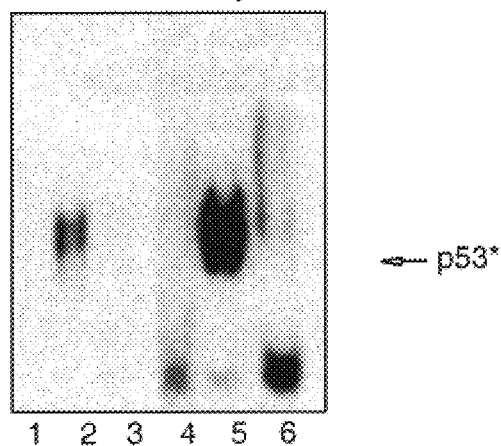

A similar analysis was carried out using DnaK activated p53 His273 and wild type p53 (FIG. 3B). After the activation by DnaK (lanes 2 and 5 vs. lanes 1 and 4), NEM inhibited sequence specific DNA binding of both mutant and wild type p53s (lanes 3 and 6), while the control reactions containing an excess of DTT were not affected by NEM (lanes 2 and 5). These results suggest that post-translational modulation of the reactive sulfhydryl group through a redox mechanism will greatly affect p53 function and imply that mutant p53 proteins are not defective in DNA binding owing to a propensity of this sulfhydryl group to exist in an oxidized state.

The Constitutively Active p53Δ30 Requires a Reactive Sulfhydryl for DNA Binding

Figure 4A:
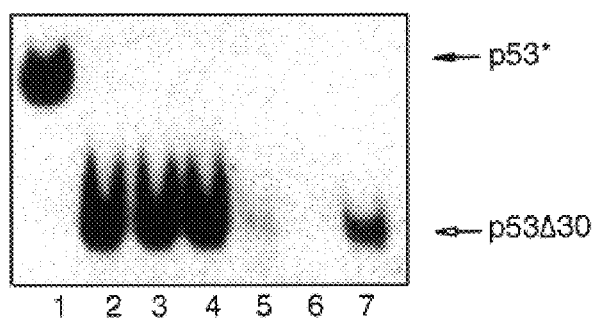
FIGS. 4A–4B: p53Δ30 DNA sequence-specific DNA binding activity is sensitive to sulfhydryl modifying reagents. (A) Sensitivity of p53Δ30 to oxidation. p53Δ30 (60 ng) was first treated with redox reagents: lane 1 (full length p53 activated by PAb421), lane 2 (p53Δ30 only), lane 3 (p53Δ30 and 2 mM DTT), lane 4 (p53Δ30 and 2 mM DTT followed by 1 mM NEM), lane 5 (p53Δ30 and 1 mM NEM followed by 2 mM DTT), lane 6 (p53Δ30 and 0.5 mM Diamide), and lane 7 (p53Δ30 and 0.5 mM Diamide followed by 2 mM DTT). (B) PAb421-activated full length p53 is sensitive to reversible oxidation by diamide. p53 (60 ng) was first activated by PAb421 as indicated in the methods and then treated with the indicated redox reagents: lane 1–4 (0.1 mM, 0.4 mM, 1.6 mM, and 5.4 mM Diamide, respectively) and lanes 5–8 (as in '1–4' but followed by the addition of DTT to 6 mM). After the modifications, p53 was assayed for sequence specific DNA binding.

Even the possibility that a reactive sulfhydryl is required at some undetected state during the activation of wild type or mutant forms of p53, we studied the effects of sulfhydryl modifying agents on p53Δ30 activity. This recombinant enzyme is constitutively active for sequence-specific DNA binding as it lacks the C-terminal 30 amino acids containing the negative regulatory motif which, in an unmodified state, prevents activity. The inclusion of NEM inhibited DNA binding of this protein as it does wild type full length activated p53 (FIG. 4A, lane 5 vs. lanes 2–4). Diamide, which unlike NEM, reversibly oxidizes sulfhydryl residues, also inactivated p53Δ30 activity (lane 6 vs. lanes 2–4). The addition of DTT to diamide-oxidized p53Δ30 reactivated the function of the protein (lane 7).

Figure 4B:
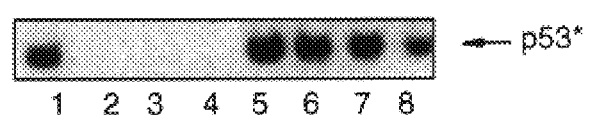

Wild type full length p53 also responded similarly to Diamide. The inclusion of increasing amounts of Diamide inactivated the DNA binding activity of PAb421-activated full length p53 (FIG. 4B, lanes 1–4). The subsequent treatment of the reactions with an excess of DTT reversed the oxidation promoted by Diamide (lanes 5–8).

Determination of the Target Site for Binding of DnaK in Relation to the Sites for PAb421 and CasKII The C-terminal 30 amino acid region of p53 is denoted by amino acid residues 363–393. We screened a series of synthetic peptides derived from the C-terminus of p53 for the ability to compete with DnaK activation of the protein. Wild type p53 was first activated for DNA binding by PAb421, DnaK and CasKII in the absence of peptides. Peptide C379–393 was unable to compete effectively with activation by PAb421 and CasKII. The PAb421 epitope is lacking in this peptide, so it was expected that it would not interfere with activation of p53. In contrast, peptide C379–393 at concentrations from 500 μM to 5 μM blocked DnaK activation. The peptide C369–383 inhibited PAb421 activation by p53, while it was ineffective at inhibiting DnaK or CasKII activation of p53 binding. This suggests that the DnaK targets the C-terminal 15 amino acids of p53, flanking the PAb421 epitope and CasKII phosphorylation sites. Peptide C374–388 could block DnaK activation as well as peptide C379–393, suggesting that the C-terminal 5 amino acids, containing the CasKII phosphorylation site, are not recognised by DnaK. The peptide C369–383 containing the PAb421 epitope removed important determinants of DnaK binding.

SUMMARY

From our studies, we have identified a class of mutant p53 which is defective in a GTP or ATP dependent post-translational activation of its sequence-specific DNA binding function by casein kinase II. However, these mutants can be converted to activated states by a distinct set of proteins, including PAb421 and *E.coli* Hsp70 (DnaK). Two important criteria appear necessary for this conversion. These modifications presumably will be relevant in the cell and include: (i) a specific, high affinity binding of an 'activating' polypeptide (or mimetic) involved in neutralization of the C-terminal negative regulatory domain; and (ii) a highly reduced environment which can maintain p53 in an activated state. Activation of mutant p53 from its cryptic state by a monoclonal antibody and a heat shock protein has tremendous therapeutic implications. Given the clear association between the DNA binding activity and tumour suppressor functions of p53, these results imply that in many tumour cells there are high levels of mutant p53 that can potentially be activated to restore significant wild type function.

Therapeutic applications of the present invention include the administration of an activating ligand for p53, or administration of a constitutively active p53, such as p53 having the C-terminal 30 amino acids deleted. The latter is based on our disclosure in Hupp et al (17) on wild-type p53, but a similar effect may be obtained with mutant p53. There is also evidence that the C-30 deleted form may be even more active in DNA binding than the PAb421 activated full length molecule.

Instead of administering these agents directly, they could be produced in the target cells by expression from an encoding gene introduced into the cells, eg in a viral vector (a variant of the VDEPT technique—see below). The vector could be targeted to the specific cells to be treated, or it could contain regulatory elements which are switched on more or less selectively in the target cells.

Alternatively, the agent (constitutively active p53 or p53-activating ligand) could be administered in a precursor or form, for conversion to the active form by an activating agent produced in, or targeted to, the cells to be treated. This type of approach is sometimes known as ADEPT or VDEPT; the former involving targeting the activating agent to the cells by conjugation to a cell-specific antibody or ligand, while the latter involves producing the activating agent, eg an enzyme, in the target cells by expression from encoding DNA in a viral vector (see for example, EP-A-415731 and WO 90/07936).

Various methods of administration of the therapeutic agent can be used, following known formulations and procedures, Dosages can be determined by routine experimentation. As noted above, administration may be systemic or targeted, the latter employing direct application of the agent to the target cells or the use of targeting systems such as antibody or cell-specific ligands. Targeting may be desirable for a variety of reasons: for example if the agent is unacceptably toxic, or if it would otherwise require too high a dosage, or if it would not otherwise be able to enter the target cells.

The normal cellular environment is sufficiently reducing for P53 to be active—see (ii) above—but there may be an enhanced effect from the administration of a reducing agent, as we have found that in tissue culture wild-type p53 can be activated by the extracellular addition of a reducing agent (dithiothreitol) to the culture medium.

REFERENCES

The following documents are hereby incorporated by reference into the present disclosure.
1. Vogelstein, B. and Kinzier, K. W. (1992) *Cell* 70, 523–526.
2. Kastan, M. B., Onyekwere, O., Sidransky, D., Vogelstein, B. and Craig, R. W. (1991) *Cancer Res.* 51, 6304–6311.
3. Livingstone, L. R., White, A., Sprouse, J., Livanos, E., Jacks, T. and Tlsty, T. D. (1992) *Cell* 70, 923–935.
4. Yin, Y., Tainsky, M. A., Bischoff, F. Z., Strong, L. C. and Wahl, G. M. (1992) *Cell* 70, 937–948.
5. Lane, D. P. and Benchimol, S. (1990) *Genes Dev.* 4, 1–8.

6. Levine, A. J., Momand, J. and Finlay, C. A. (1991) *Nature* 351, 453–456.
7. Shaulian, E., Zauberman, A., Ginsberg, D. and Oren, M. (1992) *Mol. Cell. Biol.* 12, 5581–5592.
8. Donehower, L. A., Harvey, M., Slagle, B. L., McArthur, M. J., Montgomery Jr, C. A., Butel, J. S. and Bradley, A. (1992) *Nature* 356, 215–221.
9. Malkin, D., Li, F. P., Strong, L. C., Fraumeni, J. F., Nelson, C. M., Kim, D. H., Kassel, J., Gryka, M. A., Bischoff, F. Z., Tainsky, M. A. and Friend, S. H. (1990) *Science* 250, 1233–1238.
10. Maltzman, W. and Czyzyk, L. (1984) *Mol. Cell. Biol.* 4, 1689–1694.
11. Hall, P. A., McKee, P. H., Menage, H. D., Dover, R. and Lane, D. P. (1992) *Oncogene* 8, 203–207.
12. Kern, S., Kinzler, K., Bruskin. A., Jarosz, D., Friedman, P., Prives, C., and Vogelstein, B. (1991) *Science* 252, 1708–1711.
13. Bargonetti, J., Friedman, P. N., Kern, S. E., Vogelstein. B. and Prives, C. (1991) *Cell* 65, 1083–1091.
14. Kern, S. E., Pietenpol, J. A., Thiagalingam, S., Seymour, A., Kinzler, K. W. and Vogeistein, B. (1992) *Science* 256, 827–830.
15. Scharer, E. and Iggo, R. (1992) *Nucl. Acids Res.* 20, 1539–1545.
16. Funk, W. D., Pak, D. T., Karas, R. H., Wright, W. E. and Shay, J. W. (1992) *Mol. Cell Biol.* 12, 2866–2871.
17. Hupp, T. R., Meek, D. M., Midgley, C. A. and Lane, D. P. (1992) *Cell* 71, 875–886.
18. Lane, D. P. (1992) *Nature* 358, 15–16.
19. Kastan, M. B., Zhan, Q., El-deiry, W. S., Carrier, F., Jacks, T., Walsh, W., Plunkett, B. S., Vogeistein. B. and Fornace Jr, A. J. (1992) *Cell* 71, 587–597.
20. Barak, Y., Juven, T., Haffner, R. and Oren, M. (1993) *EMBO J.* 12, 461–468.
21. El-Deiry, W. S., Kern, S. E., Pietenpol, J. A. Kinzler, K. W. and Vogeistein. B. (1992) *Nature Genetics* 1, 45–49.
22. Farmer, G. Bargonetti. J., Zhu. H., Friedman. P., Prywes, R. and Prives, C. (1992) *Nature* 358, 83–86.
23. Kern, S. E., Kinzier, K. W., Baker, S. J., Nigro, J. M., Rotter, V., Levine, A. J., Friedman, P., Prives, C. and Vogelstein, B. (1991) *Oncogene* 6, 131–136.
24. Hunter, T. and Karin, M. (1992) *Cell* 70, 375–387.
25. Meek, D. W., Simon, S., Kikkawa, U. and Eckhart, W. (1990) *EMBO J.* 9, 3253–3260.
26. Milne, D. M. Palmer, R. H., Campbell, D. G. and Meek, D. W. (1992) *Oncogene* 7, 1361–1370.
27. Lees-Miller, S. P. Chen, Y., and Anderson, C. W. (1990) *Mol. Cell. Biol.* 10, 6472–6481.
28. Meisner, M. and Czech, M. P. (1991) *Curr. Opin. Cell Biol.* 3, 474–483.
29. Carroll, D., Santoro, N. and Marshak, D. R. (1988) *Cold Spring Harbor Symp. Quant. Biol.* 53, 91–95.
30. Milne, D. M., Palmer, R. H. and Meek, D. W. (1992) *Nucl. Acids Res.* 20, 5565–5570.
31. Oliner, J. D., Kinzier, K. W., Meltzer, P. S., George, D. L. and Vogelstein, B. (1992) *Nature* 358, 80–83.
32. Shaw, P., Bovey, R., Tardy, S., Sahli, R., Sordat, B., Costa, J. (1992) *Proc. Natl. Acad. Sci. USA* 89: 4495–4499.
33. Yonish-Rouach, E., Grunwald, D., Wilder, S., Kimchi, A., May, E., Lawrence, J. J., May, P., and Oren, M. (1993) *Mol. Cell. Biol.* 13, 1415–1423.
34. Pinna, L. A. (1990) *Biochem. Biophys. Acta* 1054, 267–284.
35. Clarke, C. F. Cheng, K., Frey, A. B., Stein. R., Hinds, P. W. and Levine, A. J. (1988) *Mol.Cell.Biol.* 8, 1206–1215.
36. Hainaut, P. and Milner, J. (1992) *EMBO J.* 11, 3513–3520.
37. Kraiss, S., Quaiser, A., Oren, M. and Montenarh, M. (1988) *J. Virol.* 62, 4737–4744.
38. Sturzbecher, H.-W., Brain, R., Maimets, T., Addison, C., Rudge, K. and Jenkins, J. R. (1992) *Oncogene* 7, 1515–1523.
39. Milner, J. and Medcalf, E. A. (1991) *Cell* 65, 765–774.
40. Seto, E., Usheva, A., Zambetti, G. P., Momand, J., Horikoshi, N., Weintnann. R., Levine, A. J. and Shenk, T. (1992) *Proc. Natl. Acad. Sci. USA* 89, 12028–12032.
41. Xanthoudaxis, S., Miao, G., Wang, F., E.Pan, Y. C. and Curran, T. (1992) *EMBO J.* 11, 3323–3335.
42. McBride, A. A., Klausner, R. D. and Howley, P. M. (1992. *Proc. Natl. Acad. Sci. USA* 89, 7531–7535.
43. Abate, C., Patel, L., Rauscher, F. J. III, and Curran, T. (1990) *Science* 249, 1157–1161.
44. Xanthoudakis, S. and Curran, T. (1992) *EMBO J.* 11, 653–665.
45. Lamb, P. and Crawford, L. (1986) *Mol. Cell. Biol.* 6, 1379–1385.
46. Soussi, T., Caron de Fromentel, C., and May, P. (1990) *Oncogene* 5, 945–952.
47. Bischoff, J. R., Casso, D. and Beach, D. (1992) *Mol. Cell. Biol.* 12, 1405–1411.
48. Wade-Evans, A. and Jenkins, J. R. (1985) *EMBO J.* 4, 699–706.
49. Hwang, D. S. and Kaguni, J. M. (1991) *J. Biol. Chem.* 265, 19244–19248.
50. Mulner-Lorillon, O., Cormier, P., Labbe, J., Doree, M., Poulhe, R., Osborne, H., and Belle, R.(1990) *Eur. J. Biochem.* 93, 529–534.
51. Kandror, K., Benumov, A., and Stepanov, A. (1989) *Eur. J. Biochem.* 180, 441–448.
52. Lane, D. P. (1993) *Nature* 362, 386–387.
53. Baudier, J, Delphin, C., Grunwald, D., Khochbin, S., and Lawrence, J. J. (1992) *Proc. Natl. Acad. Sci. U.S.A.* 89, 11627–11631.
54. Friedman, P. N., Chen, X., Bargonetti, I., and Prives, C. (1993) *Proc. Natl. Acad. Sci. U.S.A.* 90, 3319–3323.
55. Borellini, F., and Glazer, R. I. (1993) *J. Biol. Chem.* 268, 7923–7928.
56. Lu, X., Park, S. H., Thompson, T. C., and Lane, D. P. (1992) *Cell* 70, 153—161.

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 11 amino acids
      (B) TYPE: amino acid (C) STRANDEDNESS: unknown
            (D) TOPOLOGY: unknown (ii) MOLECULE TYPE: peptide (xi) SEQUENCE DESCRIPTION: SEQ ID NO:1:

Ser Lys Lys Gly Gln Ser Thr Ser Arg His Lys
1               5                   10

(2) INFORMATION FOR SEQ ID NO:2:

(i) SEQUENCE CHARACTERISTICS:
            (A) LENGTH: 11 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:2:

Arg His Lys Lys Leu Met Phe Thr Lys Thr Glu
1               5                   10

(2) INFORMATION FOR SEQ ID NO:3:

(i) SEQUENCE CHARACTERISTICS:
            (A) LENGTH: 30 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:3:

Ala His Ser Ser His Leu Lys Ser Lys Lys Gly Gln Ser Thr Ser Arg
1               5                   10                  15

His Lys Lys Leu Met Phe Lys Thr Glu Gly Pro Asp Ser Asp
            20                  25                  30

(2) INFORMATION FOR SEQ ID NO:4:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:4:

AGCTTAGACA TGCCTAGACA TGCCTA                                            26

(2) INFORMATION FOR SEQ ID NO:5:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

AGCTTAGGCA TGTCTAGGCA TGTCTA                                            26

```
(2) INFORMATION FOR SEQ ID NO:6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TATGTCTAAG GGACCTGCGG TTGGCATTGA TCTTG                                    35

(2) INFORMATION FOR SEQ ID NO:7:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GTGCCAAGAT CAATGCCAAC CGCAGGTCCC TTAGACA                                  37

(2) INFORMATION FOR SEQ ID NO:8:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

RRRCWWGYY                                                                  9
```

What is claimed is:

1. A method of activating a mutant p53 protein for specific DNA binding, said method comprising contacting said mutant p53 protein with a ligand which binds within the C-terminal 30 amino acids of said mutant p53 protein within an amino acid motif bound by monoclonal antibody PAb421 or an amino acid motif bound by bacterial heat shock protein DnaK, wherein said mutant p53 protein:
   (i) occurs at elevated levels in tumors,
   (ii) does not substantially suppress tumor growth,
   (iii) is not substantially activated by CasKII mediated phosphorylation, and
   (iv) is a mutant which is latent for specific DNA binding, wherein said ligand binds within the C-terminal 30 amino acids of said mutant p53 protein, thereby activating said mutant p53 protein for specific DNA binding.

2. The method according to claim 1, wherein said ligand is monoclonal antibody PAb421 or bacterial heat shock protein DnaK.

3. The method according to claim 1, wherein said mutant p53 protein comprises at least one amino acid substitution of the wild-type p53 protein sequence outside the C-terminal 30 amino acids.

4. The method according to claim 3, wherein said at least one amino acid substitution is at either or both of amino acids 273 or 285.

5. The method according to claim 4, wherein said at least one amino acid substitution gives his273.

6. The method according to claim 4, wherein said at least one amino acid substitution gives lys285.

7. A method of activating a mutant p53 protein for specific DNA binding, said method comprising deleting a negative regulatory domain from within the C-terminal 30 amino acids of said mutant p53 protein, wherein said mutant p53 protein:
   (i) occurs at elevated levels in tumors,
   (ii) does not substantially suppress tumor growth,
   (iii) is not substantially activated by CasKII mediated phosphorylation, and
   (iv) is a mutant which is latent for specific DNA binding, wherein said step of deleting a negative regulatory domain from within the C-terminal 30 amino acids of said mutant p53 protein activates said mutant p53 protein for specific DNA binding.

8. The method according to claim 7, wherein said mutant p53 protein comprises at least one amino acid substitution of the wild-type p53 protein sequence outside the C-terminal 30 amino acids.

9. The method according to claim 8, wherein said at least one amino acid substitution is at either or both of amino acids 273 or 285.

10. The method according to claim 9, wherein said at least one amino acid substitution gives his273.

11. The method according to claim 9, wherein said at least one amino acid substitution gives lys285.

12. A p53 protein that is activated for specific DNA binding, wherein the activation of said p53 protein is obtained by the binding of a ligand within the C-terminal 30 amino acids of a mutant p53 protein within an amino acid motif bound by monoclonal antibody PAb421 or an amino acid motif bound by bacterial heat shock protein DnaK or by the deletion of a negative regulatory domain within said C-terminal 30 amino acids of said mutant p53 protein.

13. The activated p53 protein according to claim 12, wherein said ligand is monoclonal antibody PAb421 or bacterial heat shock protein DnaK.

14. The activated p53 protein according to claim 12, wherein said mutant p53 protein comprises at least one amino acid substitution of the wild-type p53 protein sequence outside the C-terminal 30 amino acids.

15. The activated p53 protein according to claim 14, wherein said at least one amino acid substitution is at either or both of amino acids 273 or 285.

16. The activated p53 protein according to claim 15, wherein said at least one amino acid substitution gives his273.

17. The activated p53 protein according to claim 15, wherein said at least one amino acid substitution gives lys285.

* * * * *